United States Patent [19]

Dahl et al.

[11] Patent Number: 4,868,271

[45] Date of Patent: Sep. 19, 1989

[54] NOVEL AROMATIC POLYMERS

[75] Inventors: Klaus J. Dahl, Atherton; Patrick J. Horner, Menlo Park; Heinrich C. Gors, Mountain View; Viktors Jansons, Los Gatos, all of Calif.; Richard H. Whiteley, Wiltshire, United Kingdom

[73] Assignee: Raychem Corporation, Menlo Park, Calif.

[21] Appl. No.: 790,286

[22] Filed: Oct. 22, 1985

[51] Int. Cl.⁴ .................. C08G 8/02; C08G 14/00
[52] U.S. Cl. ........................ 528/171; 528/125; 528/126; 528/128; 528/172; 528/360; 528/361
[58] Field of Search ............... 528/171, 128, 172, 125, 528/126, 360, 361

[56] References Cited

U.S. PATENT DOCUMENTS

| | | | |
|---|---|---|---|
| 3,705,870 | 12/1972 | Darmory et al. | 528/353 |
| 3,809,682 | 5/1974 | Studinka et al. | |
| 3,838,097 | 9/1974 | Wirth et al. | |
| 3,914,298 | 10/1975 | Dahl . | |
| 3,956,240 | 5/1976 | Dahl et al. | |
| 4,036,815 | 7/1977 | Feasey et al. | |
| 4,108,837 | 8/1978 | Johnson et al. | |
| 4,178,428 | 11/1979 | Arnold et al. | 528/174 |
| 4,218,555 | 8/1980 | Antonoplos et al. | 528/125 |
| 4,229,564 | 10/1980 | Dahl | 528/175 |
| 4,239,884 | 12/1980 | Dahl . | |
| 4,247,682 | 1/1981 | Dahl . | |
| 4,296,217 | 10/1981 | Stuart-Webb . | |
| 4,316,844 | 2/1982 | Waitkus et al. | 528/185 |
| 4,324,881 | 4/1982 | Blinne et al. | 528/173 |
| 4,356,298 | 10/1982 | Marvel et al. | |
| 4,414,269 | 11/1983 | Lubowitz et al. | |
| 4,476,184 | 10/1984 | Lubowitz et al. | |
| 4,513,131 | 4/1985 | Reinhardt et al. | |
| 4,540,748 | 9/1985 | Matzner et al. | |
| 4,619,975 | 10/1986 | Matzner et al. | |
| 4,642,327 | 2/1987 | Matzner et al. | |
| 4,668,744 | 5/1987 | Matzner et al. | |

OTHER PUBLICATIONS

Coulehan et al., Polym. Prepr. 12(1), 305 (1971).
Jin et al., Brit. Polym. J. 1980, 132.

*Primary Examiner*—John Kight
*Assistant Examiner*—M. L. Moore
*Attorney, Agent, or Firm*—Yuan Chao; Edith A. Rice; Herbert G. Burkard

[57] ABSTRACT

Novel aromatic poly(ether ketones) having imide, amide, ester, azo, quinoxaline, benzimidazole, benzoxazole, or benzothiazole groups, comprising, for example, a repeat unit

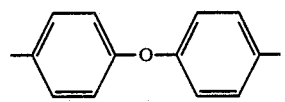

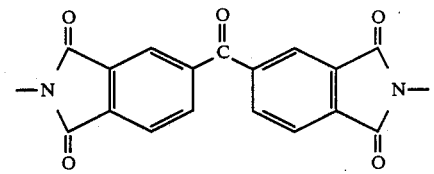

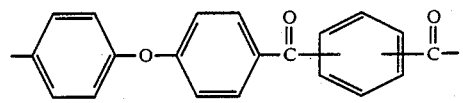

are prepared by Friedel Crafts polymerization.

4 Claims, No Drawings

NOVEL AROMATIC POLYMERS

This application is a continuation-in-part of application Ser. No. 755,941, filed July 16, 1985 now abandoned, which is a continuation-in-part of application Ser. No. 659,599, filed Oct. 11, 1984, now abandoned.

BACKGROUND OF THE INVENTION

This invention relates to novel aromatic poly(ether ketones) having imide, amide, ester, azo, quinoxaline, benzimidazole, benzoxazole, or benzothiazole groups and to methods for their preparation, particularly to electrophilic polymerization in the presence of a Lewis acid and a complex between a Lewis acid component and a Lewis base component and, optionally, a diluent.

Aromatic poly(ether ketones), in particular those wherein the aromatic groups are all para-linked, possess many desirable properties, for example, high temperature stability, mechanical strength, and resistance towards common solvents. Unlike many other "high temperature stable" polymers, they are melt processable on conventional euqipment.

It has now been discovered that the incorporation of imide, amide, ester, azo, quinoxaline, benzimidazole, benzoxazole, or benzothiazole groups into an aromatic poly(ether ketone) results in a polymer having surprisingly superior properties over known aromatic poly(ether ketones). Further, the resulting polymer has unexpectedly superior properties or processability compared to aromatic polymers having imide, amide, ester, azo, quinoxaline, benzimidazole, benzoxazole, or benzothiazole groups. Methods for preparing aromatic poly(ether ketones) having functional groups such as amide, ester, imide, azo, benzimidazole, benzothiazole, benzoxazole, quinoxaline, and the like have also been discovered.

Aromatic poly(ether ketones) can be prepared by Friedel Crafts synthesis in which an aryl ketone linkage is formed from a carboxylic acid halide and an aromatic compound having an activated hydrogen, i.e., a hydrogen atom displaceable under the electrophilic reaction conditions. The monomer system employed in the reaction can be, for example, (a) a single aromatic compound containing a carboxylic acid halide as well as an aromatic carbon bearing a hydrogen activated towards electrophilic substitution; or (b) a two-monomer system of a dicarboxylic acid dihalide and an aromatic compound containing two such activated hydrogens.

A common medium for such Friedel Crafts reactions consists of the reactant(s), a catalyst, such as anhydrous aluminum chloride, and an inert solvent such as methylene chloride. Because carbonyl groups complex with aluminum trichloride and thereby deactivate it, the aluminum chloride catalyst is generally employed in the preparation of arylene ketones in an amount slightly more than one equivalent for each equivalent of carbonyl groups in the reaction medium. The slight excess assures that enough free aluminum chloride will be present to fulfill its catalytic role. Other metal halides such as ferric chloride may be employed as the catalyst, but generally with less satisfactory results.

SUMMARY OF THE INVENTION

This invention provides polymers comprising a repeat unit

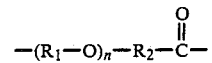

wherein $R_1$ is independently p-phenylene or 4,4'-biphenylene; $R_2$ is

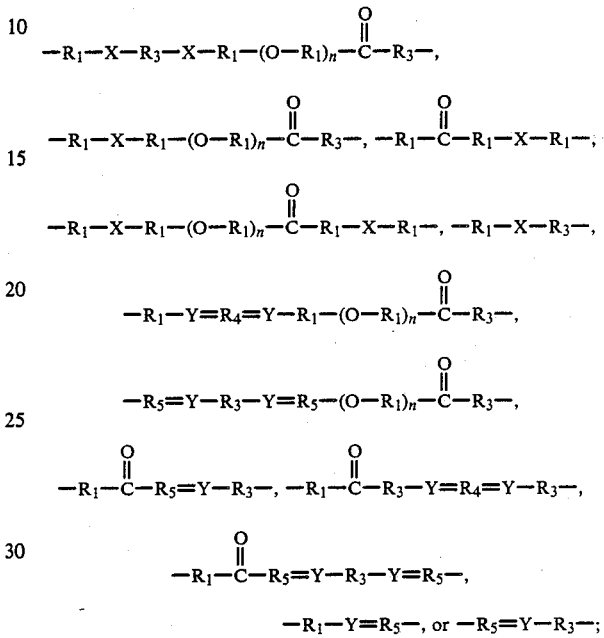

$R_3$ is independently $C_1$ to $C_{12}$ alkylene or fluorinated alkylene or substituted or unsubstituted p-phenylene, m-phenylene, 1,4-naphthylene, 2,6-naphthylene, 2,6-pyridinediyl, 2,5-pyridinediyl, or

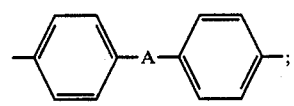

$R_4$ is substituted or unsubstituted

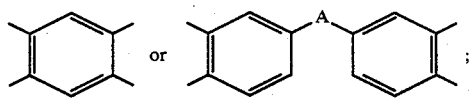

$R_5$ is independently substituted or unsubstituted

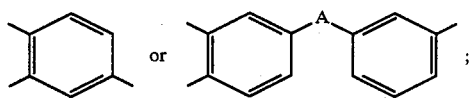

X is independently ester, amide, or azo; Y is independently

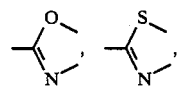

-continued

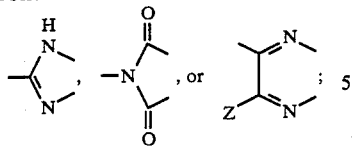

A is independently ether, ketone, sulfone, C₁ to C₁₂ alkylene or fluorinated alkylene, thioether, hexafluoroisopropylidene, isopropylidene, or a direct bond; Z is independently hydrogen, phenyl, or lower alkyl; and n is 1 or 2.

According to another aspect of this invention, there is provided a process for preparing aromatic poly(ether ketones) having an imide, amide, ester, azo, quinoxaline, benzimidazole, benzoxazole, or benzothiazole group, comprising polymerizing a monomer system selected from the group consisting of (I) a self polymerizing monomer having a carboxylic acid halide group, a hydrogen activated towards electrophilic substitution, and an imide, amide, ester, azo, quinoxaline, benzimidazole, benzoxazole, or benzothiazole group;

(II) substantially stoichiometric amounts of an aromatic dicarboxylic acid dihalide and an aromatic compound having two hydrogens activated towards electrophilic substitution, provided at least one of said acid dihalide and said aromatic compound has an imide, amide, ester, azo, quinoxaline, benzimidazole, benzoxazole, or benzothiazole group; and (III) combinations of the above;

in a reaction medium comprising (A) a Lewis base in an amount from 0.01 to 4 equivalents per equivalent of acid halide groups present in said monomer system;

(B) a Lewis acid in an amount of about one equivalent per equivalent of carbonyl groups present plus one equivalent per equivalent of Lewis base, plus an amount effective to act as a catalyst for said polymerization; and (C) a non-protic diluent in an amount from 0 to 93 percent by weight, based on the weight of the total reaction mixture.

DETAILED DESCRIPTION OF THE INVENTION

This invention provides aromatic poly(ether ketones) having imide, amide, ester, azo, quinoxaline, benzimidazole, benzoxazole, or benzothiazole groups. A preferred method for making these polymers is Friedel Crafts polymerization, in which the polymerization step consists of the reaction of a carboxylic acid halide with an aromatic group having a hydrogen activated towards electrophilic substitution to form a diaryl ketone. Particularly preferred is Friedel Crafts polymerization in the presence of excess Lewis acid and a complex between a Lewis acid and a Lewis base.

Monomer systems suitable for the preparation of the polymers of this invention by Friedel Crafts polymerization are of two general types. The first, which will be called the one monomer system, comprises an aromatic compound having both a carboxylic acid halide and a hydrogen atom activated towards electrophilic substitution. Such a monomer is called an EN monomer because it has both an electrophilic group (the carboxylic acid halide) and a nucleophilic group (the aromatic group having the activated hydrogen). The following examples of EN monomers are illustrative but not exhaustive:

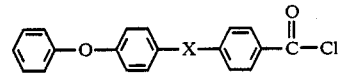

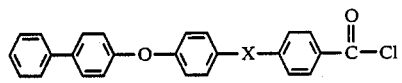

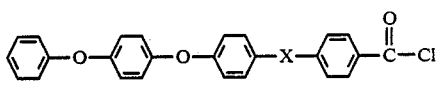

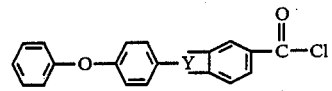

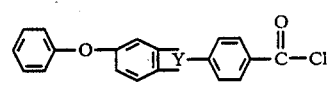

where X is independently amide, ester, or azo and where Y is independently

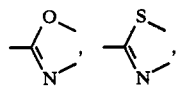

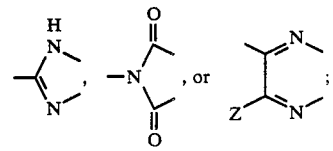

where Z is independently hydrogen, phenyl, or lower alkyl.

Polymers of this invention which can be prepared from EN monomers include, for example

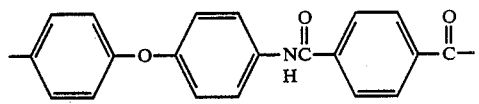

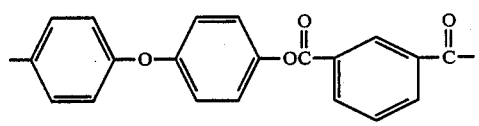

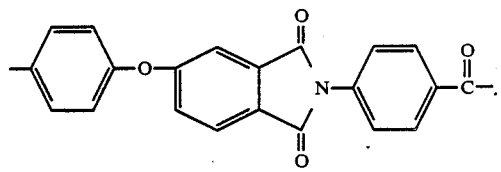

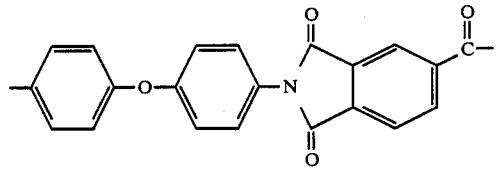

The second monomer system, which will be called the two monomer system, comprises a dicarboxylic acid dihalide and an aromatic compound having two hydrogen atoms activated towards electrophilic substitution. In keeping with the above shorthand notation, these are called the EE and NN monomers, respectively. Where a high degree of polymerization is desired, the EE and NN monomers should be present in substantially stoichiometric amounts. Illustrative but not exhaustive examples of EE monomers are:

or fluorinated alkylene, thioether, isopropylidene, hexafluoroisopropylidene, or a direct bond and where

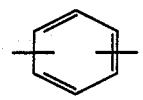

denotes meta- or para-phenylene.

Illustrative but not exhaustive examples of NN mono-

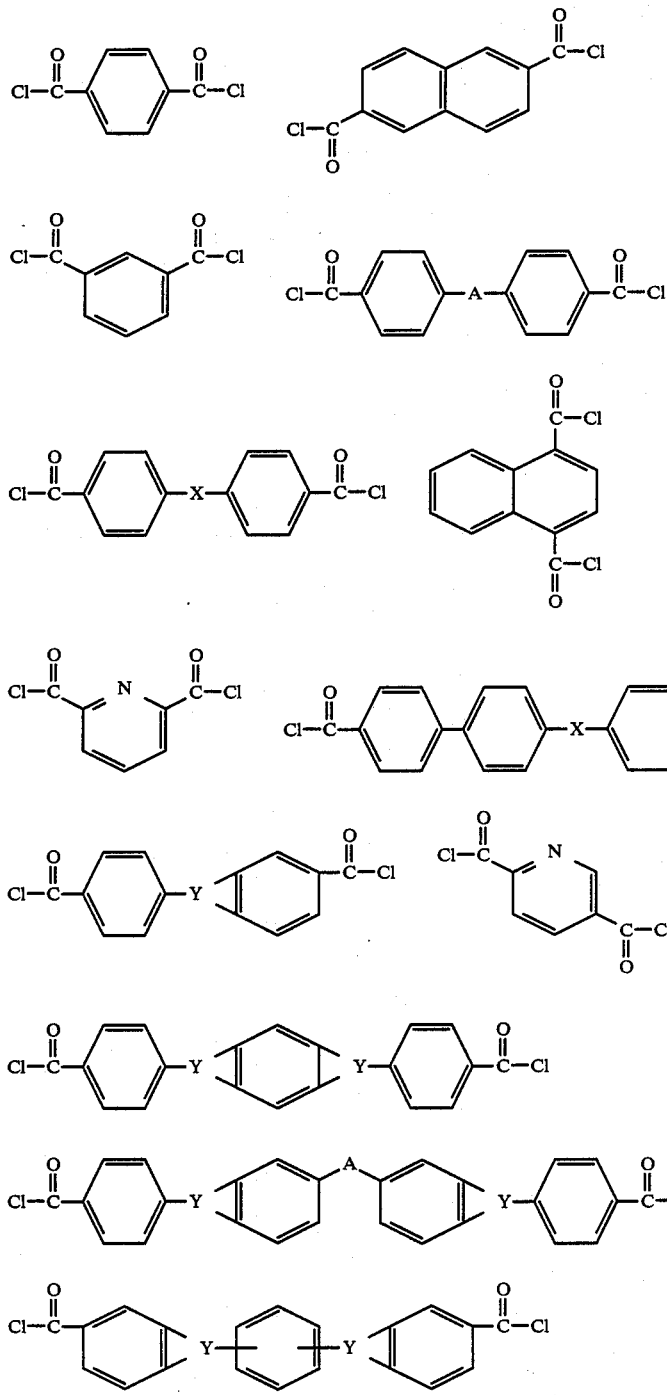

where X and Y are as hereinbefore defined and A is independently ether, ketone, sulfone, $C_1$ to $C_{12}$ alkylene mers are:

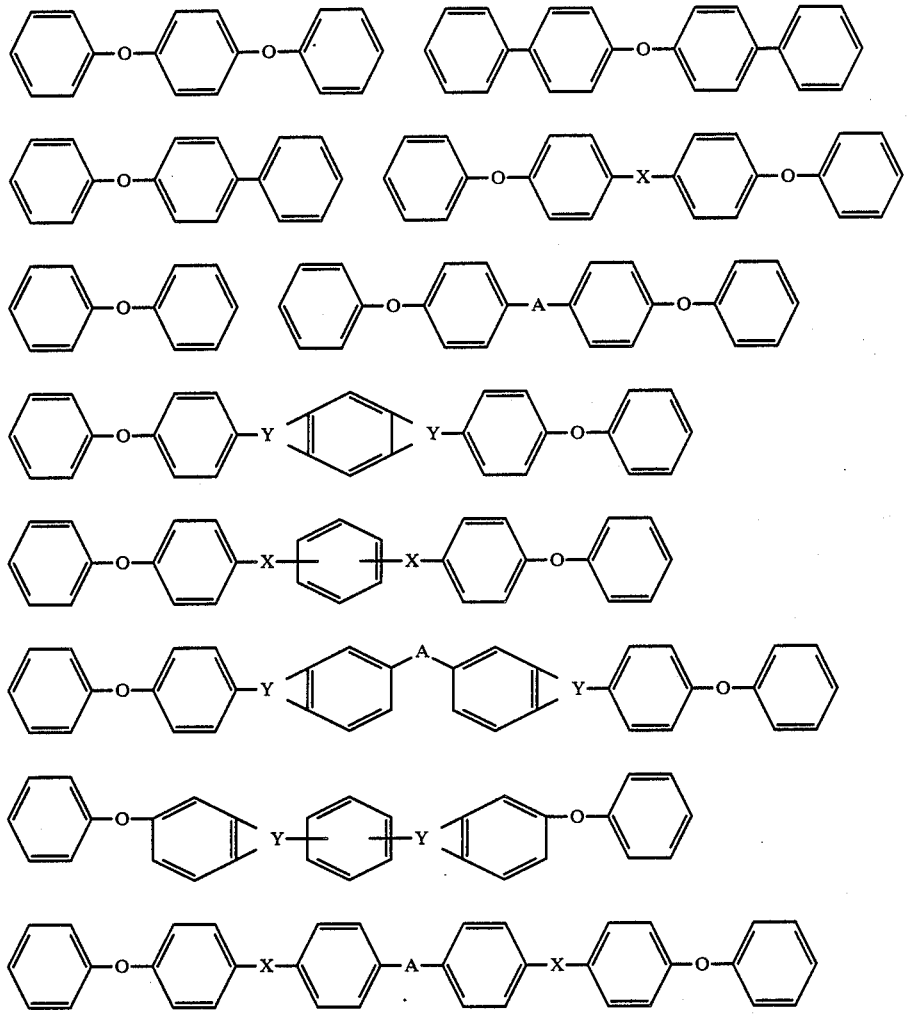
where A, X, and Y are as hereinbefore defined.
It is evident that if an EE monomer having no X or Y groups is selected, it should be polymerized with an NN monomer having an X or Y group, and vice-versa. Alternatively, both EE and NN can have an X or Y group. Examples of polymers which can be prepared in such a manner include
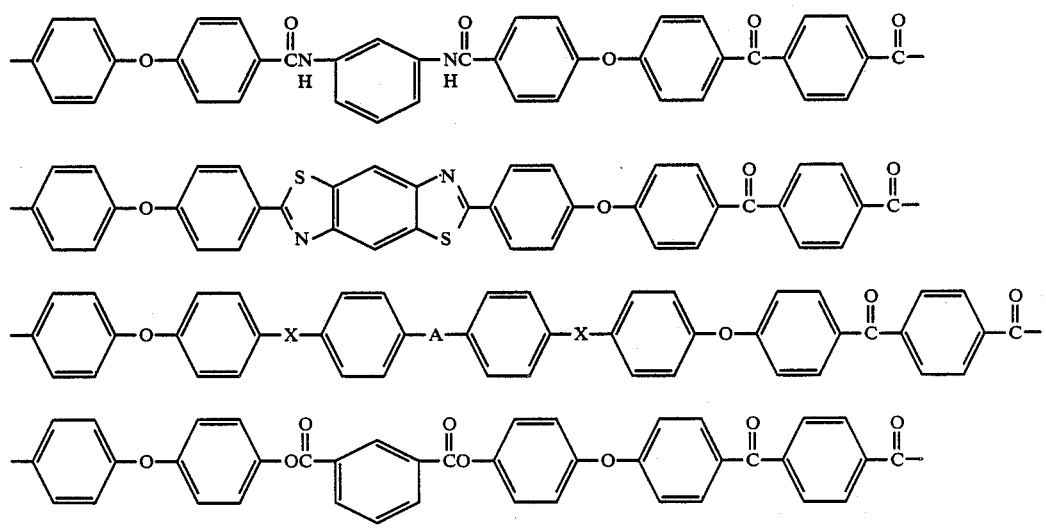

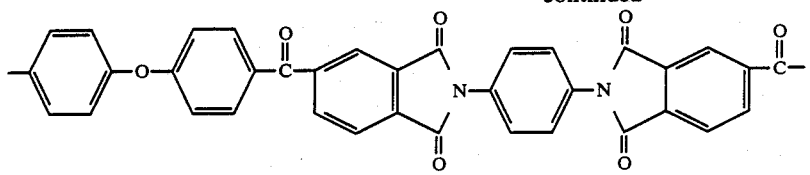

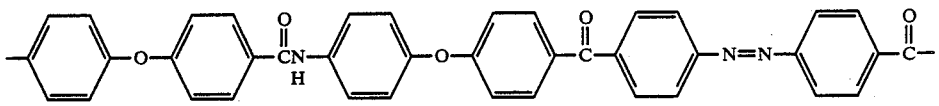

In the preceding illustrations of suitable monomers, the carboxylic acid halides were consistently represented as the chloride as a matter of convenience. It will be apparent to one skilled in the art that the acid fluoride and the acid bromide are also suitable. Also, as a matter of convenience, aromatic rings have been drawn as unsubstituted, although it will be apparent to one skilled in the art that they may have one or more substituents which are inert under the polymerization conditions and which do not interfere with the polymerization. Examples of such substituents include lower alkyl, particularly methyl; cyano; halogen, particularly fluoro, bromo and chloro; nitro; and benzoyl. Substituents forming crosslinks or branches under the polymerization conditions should be avoided unless crosslinked or branched polymer is desired. Finally, it should be cautioned that substitution is generally undesirable on a ring containing a hydrogen activated toward electrophilic substitution, as substituents tend to interfere with the polymerization.

It is contemplated that the polymers of this invention include copolymers. For example, two or more different EN monomers may be copolymerized. Or a single EE monomer can be copolymerized with two or more different NN monomers. Or one or more EN monomers can be polymerized with combinations of EE and NN monomers. To illustrate,

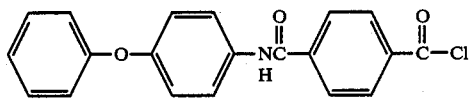

and

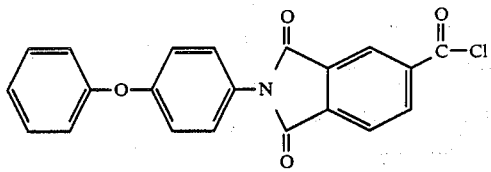

may be copolymerized to yield a copolymer with the repeat units

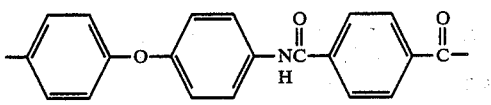

and

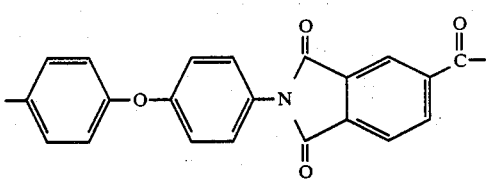

Furthermore, it is also contemplated that the polymers of this invention include copolymers with prior art poly(ether ketones). Among the latter, the repeat units of particular interest for incorporation into copolymers are

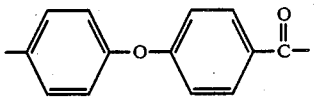

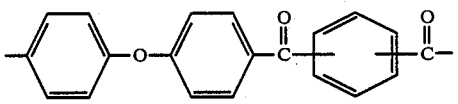

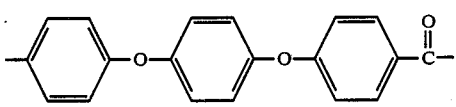

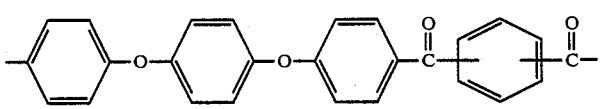

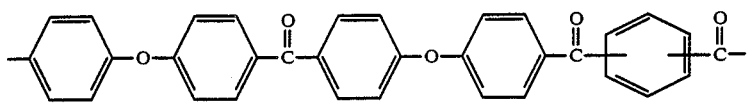

The synthesis of these prior art poly(ether ketones) is described in Bonner, U.S. Pat. No. 3,065,205; Dahl, U.S. Pat. No. 3,953,400; Dahl et al, U.S. Pat. No. 3,956,240; and Jansons et al., PCT Application WO 84/03891. To illustrate,

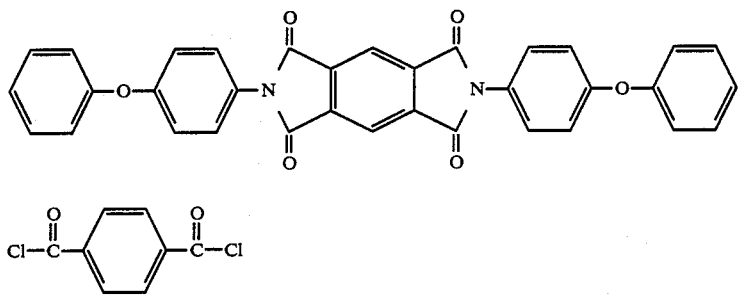

can be copolymerized to yield a copolymer with the repeat units

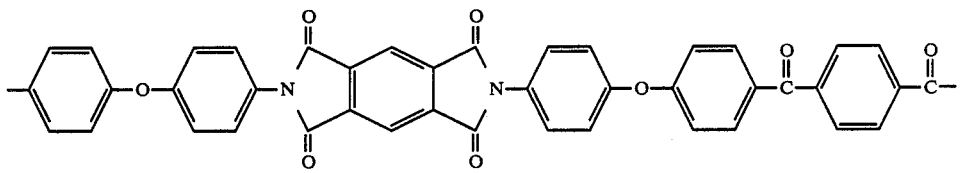

and

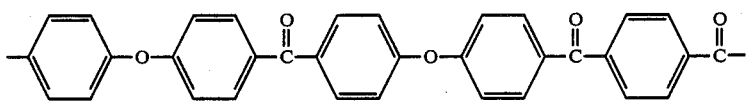

As with other electrophilic polymerizations, the monomer(s) used should be relatively free of any impurities which would interefere with the polymerization.

As used in this specification, a "hydrogen activated towards electrophilic substitution" is a hydrogen bonded to an aromatic carbon atom and displaceable by an acyl group under the well-known conditions for Friedel Crafts acylation to occur. In particular, it is displaceable under the reaction conditions of this invention. A hydrogen is activated for a Friedel Crafts reaction by the presence of an electron donating group ortho or para to it. Particularly desirable activated hydrogen bearing aromatic moieties are phenoxy ($C_6H_5O$—) and p-biphenyloxy ($C_6H_5$—p—$C_6H_4$—O—).

Those skilled in the art will readily realize that in Friedel Crafts acylations and polymerizations, involving, for example, the phenoxy group, reaction may take place at one of three positions: either of the two ortho positions or the para position. However, once one acylation has occurred, the just-introduced acyl group exerts a deactivating effect which inhibits further reaction in the phenoxy group. Thus, for stoichiometric purposes, a phenoxy group is deemed to have only one activated hydrogen. It has been our experience that reaction generally takes place at the para-position (i.e., it is the para-hydrogen that is "activated"), particularly where the polymerization is run in the presence of a Lewis acid and a complex between a Lewis acid and a Lewis base, as taught hereinafter.

A preferred process for preparing the polymers of the instant invention comprises the use of a reaction medium comprising free Lewis acid and a complex between a Lewis acid and a Lewis base and, optionally, a diluent. The term "complex" is used to mean any product of the reaction between the Lewis acid and the Lewis base. A diluent is employed if the complex is a solid at polymerization temperatures and can be present, if desired, when the complex is liquid.

The term "Lewis acid" is used herein to refer to a substance which can accept an unshared electron pair from another molecule. Lewis acids which can be used in the practice of this invention include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. The use of substantially anhydrous aluminum trichloride as the Lewis acid is preferred.

The amount of Lewis acid used in the practice of this invention varies depending on the particular monomers and reaction medium selected. In all instances at least about one equivalent of Lewis acid per equivalent of carbonyl groups present in the monomer system is used plus an amount effective to act as a catalyst for the reaction (also referred to herein as a catalytic amount). Generally a catalytic amount added is from about 0.05 to about 0.3 equivalents of Lewis acid per equivalent of acid halide in the reaction mixture. Additional amounts of Lewis acid are also required depending on the nature of the monomers and the reaction conditions in a manner as set forth below. Further, if a comonomer containing other basic species is used, additional Lewis acid may be required.

In a preferred embodiment of the invention, the reaction is controlled by the addition of a controlling agent which, inter alia, suppresses undesirable side reactions, particularly alkylation and/or ortho substitution of activated aryl groups. Suppression of side reactions results in polymer that can that will be more readily melt processable because it will be less likely to degrade or cross-link when subjected to elevated temperatures, e.g. temperatures above its melting point. For a polymer of this type to be suitable for melt processing, it must be able to withstand the processing temperatures for the required processing time. Typically these conditions require that the polymer can withstand temperatures up to about 30° C. above the melting or softening point of the polymer for periods of at least 30 minutes, preferably at least 60 minutes and most preferably at least 90 minutes, without undesired gel formation or substantial change in inherent viscosity.

Preferred controlling agents for the polymerization are Lewis bases. The term "Lewis base" is used herein to refer to a substance capable of donating an unshared electron pair to a Lewis acid. Thus, the Lewis base forms a complex with the Lewis acid used in the reaction medium. It has been found that Lewis bases which form a 1:1 complex having a heat of association at least about that of diphenyl ether with the Lewis acid are preferred. For example, where aluminum trichloride is the Lewis acid the Lewis base used should form a 1:1 complex having a heat of association of at least about 15 kcal/mole, preferably at least about 20 kcal/mole and most preferably at least about 30 kcal/mole. While the heats of association are for a 1:1 Lewis acid/Lewis base complex consisting solely of these two components, the actual complex formed in the reaction medium need not be a 1:1 complex. A discussion on heats of association for Lewis acid/Lewis base complex is found in J. Chem. Soc. (A), 1971, pages 3132-3135 (D. E. H. Jones et al). The Lewis base used should not be an acylating, alkylating agent nor should it be acylatable under the reaction conditions. Mixtures of two or more Lewis bases can be used if desired. The Lewis base used as a controlling agent in the practice of this invention is an additional component added to the reaction medium. This does not include basic species formed in situ during the reaction.

Typical Lewis bases which can be employed include, for example, amides, amines, esters, ethers, ketones, nitriles, nitro compounds, phosphines, phosphine oxides, phosphoramides, sulfides, sulfones, sulfonamides, sulfoxides and halide salts.

Examples of specific organic Lewis bases that can be used in the practice of this invention are acetone, benzophenone, cyclohexanone, methyl acetate, ethylene carbonate, N-methyl-formamide, acetamide, N,N-dimethylacetamide, N-methylpyrrolidone, urea, tetramethylurea, N-acetylmorpholine, dimethyl sulfoxide, N,N-dimethylformamide, diphenyl sulfone, N,N-dimethylmethane-sulfonamide, phosphoryl chloride, phenylphosphonyl chloride, pyridine-N-oxide, triphenylphosphine oxide, trioctylphosphine oxide, nitropropane, nitrobenzene, benzonitrile, n-butyronitrile, methyl ether, tetrahydrofuran, dimethyl sulfide, trimethylamine, N,N,N',N'-tetramethylethylenediamine, N,N-dimethyldodecylamine, imidazole, pyridine, quinoline, isoquinoline, benzimidazole, 2,2'-bipyridine, o-phenanthroline, 4-dimethylaminopyridine, and the like. In addition to covalent organic compounds, suitable Lewis bases include inorganic salts which can form complexes with Lewis acids, for example, chlorides, such as trimethylammonium chloride, tetramethylammonium chloride, sodium chloride or lithium chloride, perchlorates, trifluoro-methanesulfonates and the like.

Preferred Lewis bases for the reaction medium of this invention are N,-methylformamide, N,N-dimethyl-formamide, N,N-dimethylacetamide, 1-methyl-2-pyrrolidone, tetramethylene sulfone (also known as sulfolane), n-butyroni-trile, dimethyl sulfide, imidazole, acetone, benzophenone, trimethylamine, trimethylamine hydrochloride, tetramethyl-ammonium chloride, pyridine-N-oxide, 1-ethylpyridinium chloride, lithium chloride, lithium bromide, sodium chloride, sodium bromide, potassium chloride, potassium bromide and mixtures thereof.

The amount of Lewis base present should be from 0.01 to about 4 equivalents per equivalent of acid halide groups present in the monomer system. Preferably at least about 0.05 and most preferably at least about 0.5 equivalents of Lewis base per equivalent of acid halide groups present should be used. Amounts greater than 4 equivalents could be employed, if desired. However, no additional controlling effect is usually achieved by adding larger amounts. Thus, it is preferred to use no more than about 4 equivalents and generally about 2 equivalents. The particular amount of Lewis base added depends to a certain extent on the nature of the monomers present.

The temperature at which the reaction is conducted can be from about −50° C. to about +150° C. It is preferred to start the reaction at lower temperatures, for example at about −50° to about −10° C. particularly if the monomer system contains highly reactive monomers. After reaction has commenced, the temperature can be raised if desired, up to 150° C. or even higher, for example, to increase the rate of reaction. It is generally preferred to carry out the reaction at temperatures in the range of between about −30° C. and +25° C. (room temperature).

While it is not understood exactly how the Lewis base acts to control the reaction, it is believed that one or more of the following factors may be involved. The Lewis acid/Lewis base complex appears to influence the catalytic activity of Lewis acid, so as to substantially eliminate all ortho or meta acylation.

If a diluent such as methylene chloride or dichloroethane is used, the Lewis acid/Lewis base complex substantially reduces the tendency of the diluent to act as an alkylating agent by competing with the diluent for available Lewis acid and thereby suppressing alkylation of the polymer. Alkylation of the polymer in the para position caps the reaction while alkylation in the ortho position introduces undesired reactive sites in the polymer chain which can lead to branching or cross-linking.

A non-protic diluent can also be employed, if desired. Advantageously, the diluent should dissolve the Lewis acid/Lewis base complex and the resulting oligomer/Lewis acid complex but this is not an essential requirement of the diluent. It should also be relatively inert toward Friedel-Crafts reactions.

The diluent is used in an amount from 0 to 93% by weight, based on the weight of the total reaction mixture. As is known in reactions of this type, the reactions can be run neat, that is without the presence of a diluent. This is true for the process of this invention whether or not a Lewis base is used. As discussed in more detail below, it has been found that the monomer to diluent molar ratio can contribute to control of the reaction to yield the desired product.

Use of an alkylating or acylating diluent can lead to undesired side reactions as mentioned above. When such solvents are employed control of the reaction by techniques taught in this specification suppresses such alkylation or arylation. The result is a thermally stable, essentially linear polymer.

A most useful and unexpected aspect of the process described hereinbefore is that it enables the polymerization of phenyl esters, for example bis(4-phenoxyphenyl) terephthalate. Ordinarily, phenyl and other aromatic esters undergo the Fries rearrangement in the presence of a Lewis acid, particularly aluminum chloride. However, under the reaction conditions described, high molecular weight polymer, with no evidence of any Fries rearrangement having occurred, are obtained.

If desired, the molcular weight of the polymer, the degree of branching and amount of gelation can be controlled by the use of, for example, capping agents as described in U.S. Pat. No. 4,247,682 to Dahl, the disclosure of which is incorporated herein by reference. The molecular weight of the polymer can also be controlled by a reaction utilizing a two-monomer system as described above, by employing a slight excess of one of the monomers.

Capping agents, when employed, are added to the reaction medium to cap the polymer on at least one end of the chain. This terminates continued growth of that chain and controls the resulting molecular weight of the polymer, as shown by the inherent viscosity of the polymer. Judicious use of the capping agents results in a polymer within a selected narrow molecular weight range, decreased gel formation during polymerization, and decreased branching of the polymer chains and increases melt stability. Both nucleophilic and electrophilic capping agents can be used to cap the polymer at each end of the chain.

Preferred nucleophilic capping agents are 4-phenoxybenzophenone, 4-(4-phenoxyphenoxy)benzophenone, 4,4'-diphenoxybenzophenone, and the like.

Typical electrophilic capping agents are compounds of the formula

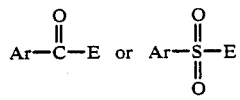

wherein Ar is phenyl, 3-chlorophenyl, 4-chlorophenyl, 4-cyanophenyl, 4-methylphenyl or an aromatic group substituted with an electron withdrawing substituent and E is halogen or other leaving group. Preferred electrophilic capping agents include benzoyl chloride, benzenesulfonyl chloride and the like.

Decomplexation of the polymer from the catalyst can be accomplished by treating the reaction mixture with a decomplexing base after completion of polymerization. The base can be added to the reaction medium or the reaction medium can be added to the base. The decomplexing base must be at least as basic towards the Lewis acid as the basic groups on the polymer chain. Such decomplexation should be effected before isolation of the polymer from the reaction mixture.

The amount of decomplexing base used should be in excess of the total amount of bound (complexed) and unbound Lewis acid present in the reaction mixture and is preferably twice the total amount of Lewis acid. Typical decomplexing bases which can be used include water, dilute aqueous hydrochloric acid, methanol, ethanol, acetone, N,N-dimethyl-formamide, N,N-dimethylacetamide, pyridine, dimethyl ether, diethyl ether, tetrahydrofuran, trimethylamine, trimethylamine hydrochloride, dimethyl sulfide, tetramethylenesulfone, benzophenone, tetramethylammonium chloride, isopropanol and the like. The decomplexed polymer can then be removed by conventional techniques such as adding a nonslvent for the polymer which is a solvent for or miscible with the Lewis acid/Lewis base complex and the Lewis acid; spraying the reaction medium into a non-solvent for the polymer; separating the polymer by filtration; or evaporating the volatiles from the reaction medium and then washing with an appropriate solvent to remove any remaining base/catalyst complex and diluent from the polymer. A method for removing the catalyst residue is described in Dahl, U.S. Pat. No. 4,239,884, the disclosure of which is incorporated by reference.

The polymers of this invention can be used in any number of ways. Because of their predominantly or wholly aromatic nature, they possess outstanding thermal stability, as evidenced by their thermogravimetric (TGA) 1% weight loss temperatures being generally above 400° C. and often above 500° C. They also possess superior mechanical properties, which are retained at elevated temperatures in view of their glass transition temperatures (Tg's) of above 150° C. Furthermore, many of these polymers are crystalline, also contributing to the maintenance of mechanical properties at elevated temperatures. Also, they possess resistance to many common solvents. Thus, the polymers of this invention are particularly suitable for use in those applications generally reserved for the so-called "heat stable" or "high performance" polymers.

The polymers of this invention, particularly the high molecular weight ones, can be used in films, filaments, electrical insulation, coatings, molded articles, and like applications. Generally, conventional fabrication techniques such as injection molding and extrusion can be used. By "high molecular weight polymer" we mean one having an inherent viscosity of 0.6 or greater.

While the process of this invention is particularly suitable for the preparation of high molecular weight polymers, low molecular weight polymers—which may be desirable for certain applications—can readily be prepared, for example by appropriate use of a capping agent or stoichiometric imbalance. The lower molecular weight polymers may be desirable for certain applications, such as adhesives or as powder coatings.

The following examples illustrate the preparation of the polymers of this invention. It is to be understood that other reactants, reaction media, and monomers within the scope of the teaching of this invention can be employed, if desired.

Reduced viscosity (RV) or inherent viscosity (IV) refer to the mean reduced viscosity or inherent viscosity, as is the case, as determined according to the method of Sorenson et al., "Preparative Methods of Polymer Chemistry," 2nd Ed., Interscience (1968), p. 44. (c=0.1 g of polymer dissolved in 100 mL of concentrated sulfuric acid at 25° C., unless noted otherwise.) Purities by differential scanning calorimetry (DSC) were estimated as described in Palermo et al., Themochim. Acta, 14, 1 (1976) and Marti, Thermochim. Acta 5, 173 (1972).

EXAMPLE 1

The bis-amide of p-phenylene diamine with p-phenoxybenzoic acid was prepared as follows.

A slurry of p-phenylene diamine (16.22 g, 0.15 mole, differential scanning calorimetry (DSC) purity >99.99%) in N,N-dimethylacetamide (DMAc, ca. 300 mL) was added to a solution of p-phenoxybenzoyl chloride (69.80 g, 0.30 mole) in DMAc (250 mL) over a 55 min period at −25° C. The mixture was allowed to warm to room temperature and stirred for about 3 days. The reaction mixture, consisting of a pale purple powder in a purple solution, was poured into water (3000 mL). The insoluble material was filtered, washed with water, and dried at 100 under a vacuum.

After decolorization with activated charcoal and two recrystallizatons from water-DMAc, 11.75 g of product was obtained. It had a mp of 322.5°–323.5° C. and was shown to be 99.93% pure by DSC. Its 300 MHz 1H-NMR spectrum was consistent with the expected structure.

EXAMPLE 2

N,N-Dimethylformamide (DMF, 2.3 mL, 2.19 g, 0.03 mole) was added with stirring and cooling to a mixture of aluminum chloride (10.3 g, 0.077 mole) in methylene chloride (50 mL). The bis-amide prepared in Example 1 (5.0032 g, 0.01000 mole) was then added. The mixture was cooled to −6° C. and terephthaloyl chloride (2.0300 g, 0.009998 mole) was added, with stirring. An intense yellow-brown colored solution with an orange-brown precipitate resulted. It was stirred at −6° C. for 15 min and then allowed to warm up to room temperature. The reaction mixture gelled after another 8 min.

The polymerization mixture was worked up by blending it with methanol (ca. 250 mL) in a Waring blender, filtering, washing with methanol (2×75 mL), and drying at 140° C.. for 4 hours in vacuum, to yield 6.00 g (95%) of fibrous pale yellow green polymer with the repeat unit

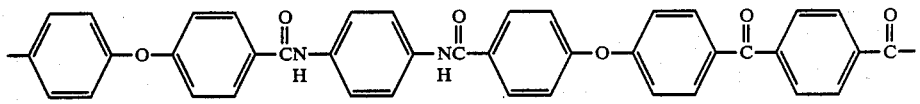

The polymer had a reduced viscosity (RV) of 0.95 dl/g in concentrated sulfuric acid (part (part of the sample did not dissolve; nominal c=0.04). The polymer was also partially soluble in DMAc/lithium bromide. GPC of such a solution showed a molecular weight spread between 30,000 and 3,000,000 (poly(ethylene oxide) equivalent molecular weight).

EXAMPLE 3

The bis-amide of m-phenylene diamine and p-phenoxybenzoic acid was prepared according to the procedure of Example 1. The product had a mp of 222–23° C. and was shown to be 99.99% pure by DSC.

EXAMPLE 4

DMF (2.2 mL, 0.0284 mole) was added with stirring and cooling to a mixture of aluminum chloride (8.3338 g, 0.0625 mole) in 1,2-dichloroethane (DCE, 40 mL). The bis-amide prepared in Example 3 (3.5039 g, 0.0070 mole) was then added, along with p-phenoxybenzophenone (0.0549 g, 0.0002 mole). The mixture was cooled to −10° C. and terephthaloyl chloride (1.4415 g, 0.0071 mole) was added, with stirring. The mixture was stirred at −10° C. for 34 min, at the end of which period an orange-brown precipitate had formed. When the reaction mixture was warmed up to room temperature, the precipitate dissolved within 5 min. After another 30 min, an orange-brown gel formed. The reaction mixture was left overnight at room temperature and then worked up as in Example 2, to yield 4.3 g (97%) of fibrous white polymer with the repeat unit

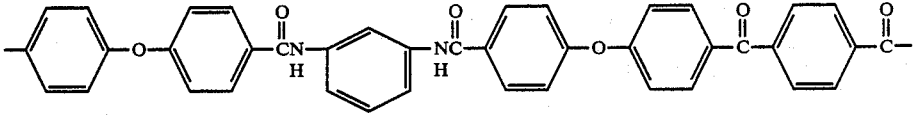

The polymer was completely soluble in concentrated sulfuric acid, from which solution a RV of 2.88 was measured (c=0.0840 g/dl).

Elemental analysis: Calc. C 76.26, H 4.16, N 4.28; Found C 74.87, H 4.20, N 4.28 (after correction for 0.24% ash)

The polymer could be hot pressed into a tough amber translucent slab at about 260° C. A sample cut from the slab had the following mechanical properties: modulus, 140,000 psi; elongation to break, 21%; ultimate tensile strength, 12,000 psi; and no yield point. When a slab was pressed at 305° C., the polymer was brittle.

TGA in air showed a 1% weight loss at 430° C. No crystallinity was detected by DSC or X-ray diffraction. A Tg of 220° C. was detected by DSC and dynamic mechanical analysis.

GPC of a DMAc-lithium bromide solution of the polymer gave the following poly(ethylene oxide)-equivalent molecular weights: Mn=99,000; Mw=214,000; Mp=152,000.

EXAMPLE 5

N,N'-Bis(4-phenoxyphenyl)pyromellitimide was prepared as follows. p-Phenoxyaniline (19.45 g, 0.105 mole, mp 82.5°-84.5° C., recrystallized from methanol-water after treatment with activated charcoal and zinc dust), pyromellitic dianhydride (10.91 g, 0.050 mole, mp 282°-284° C., purified by continuous extraction from insoluble contaminants and activated charcoal with hot 2-butanone) and glycerol (200 mL, analytical reagent grade) were stirred at 155° C. for 6 hrs under nitrogen, then cooled. The bright yellow sludge was poured into vigorously stirred water (1250 mL). The product was collected by filtration and washed successively with water, denatured alcohol, and diethyl ether. After recrystallization from DMAc, bright yellow crystals mp 382°-383.5° C. were obtained.

Elemental analysis: Calc. C 73.91, H 3.65, N 5.14; Found C 73.52, H 3.77, N 5.14

EXAMPLE 6

The pyramellitimide prepared in Example 5 (3.5915 g, 0.0065 mole) was polymerized with isophthaloyl chloride (1.3400 g, 0.0066 mole), with p-phenoxybenzophenone (0.0549 g, 0.0002 mole) as a capping agent. The amounts of aluminum chloride and DMF used were 9.654 g (0.0724 mole) and 2.05 mL (0.0264 mole), respectively. A yield of 4.32 g (96%) of yellow polymer with repeat unit

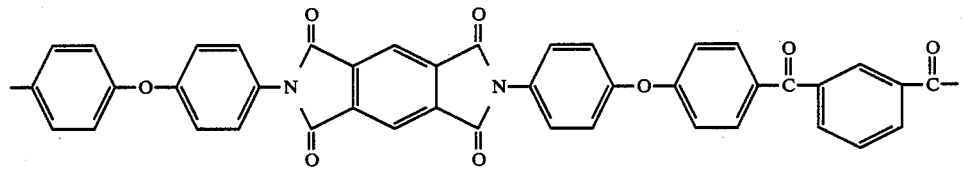

was obtained. Its RV was 0.56 (c=0.05 g/dL). TGA in air showed a 1% weight loss at 411° C.

Elemental analysis: Calc. C 74.01, H 3.27, N 4.04; Found C 73.48, H 3.36, N 4.03

EXAMPLE 7

The bis-p-phenoxybenzoate of hydroquinone was prepared by the following procedure.

Hydroquinone (5.50 g, 0.0500 mole) was stirred with heating (oil bath at 185° C.) with bis(tri-n-butyltin) oxide (29.81 g, 0.0500 mole) in xylene (225 mL of xylene was distilled off, using a Dean-Stark trap. The solution was then cooled to about 100° C. and p-phenoxybenzoyl chloride (24.43 g, 0.105 mole) in xylene (20 mL) was added. The mixture was stirred at 100° C. for 2 hr. Upon cooling, the product crystallized out.

The reaction mixture was poured into methanol (1000 mL) and the product collected by filtration, washed with methanol (2×100 mL), and dried at 100° C. for 90 min under vacuum. The yield was 22.13 g of shiny white crystals, mp 195°-197° C., 99.94% pure by DSC.

EXAMPLE 8

The bis-ester of Example 7 (3.9699 g, 0.079 mole) and terephthaloyl chloride (1.5836 g, 0.0078 mole) were polymerized by the procedure of Example 4. The amounts of aluminum chloride and DMF used were 9.19 g (0.0689 mole) and 2.40 mL (0.0312 mole), respectively. The polymer of the repeat unit

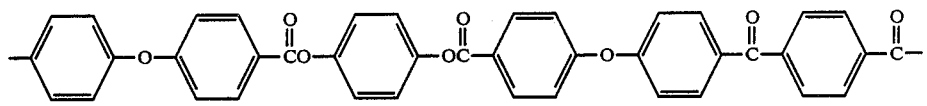

was obtained as a pale cream powder in 98% yield. It was insoluble in a variety of solvents, including DMAc, lithium chloride (3%), o-chlorophenol, chloroform, and DMSO. It was soluble in concentrated sulfuric acid, but apparently with cleavage of the ester bonds, as the measured RV was only 0.07. DSC showed a possible Tg at 161° C. TGA in air showed a 1% weight loss at 380° C.

EXAMPLE 9

The polymerization of Example 4 was repeated, but with lithium chloride (1.20 g, 0.0284 mole) used instead of DMF. The polymer (4.19 g, 93.5% yield) was obtained as cream colored fibers. Its RV was 2.17, with substantial amounts of undissolved material.

EXAMPLE 10

The polymerization of Example 8 was repeated, but with a 1:1 mixture of terephthaloyl chloride and isophthaloyl chloride instead of terephthaloyl chloride, to yield a polymer with the repeat unit

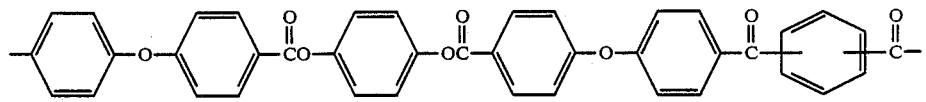

where

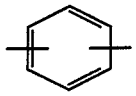

is meta- or para-phenylene.

The reduced viscosity in quinoline was 0.06 (c=0.06 g/dL), and in o-chlorophenol, 0.27 (c=0.05 g/dL). DSC showed a possible Tg at 151° C. TGA in air showed a 1% weight loss at 400° C.

EXAMPLE 11

Bis-(p-phenoxyphenyl) terephthalate was prepared from p-phenoxyphenol and terephathloyl chloride by the method of Example 7. The product was obtained in 90.6% yield, mp 192.9°–193.8° C., DSC purity 99.87%.

EXAMPLE 12

Bis-(p-phenoxyphenyl) terephthalate from Example 11 (3.8946 g, 0.00775 mole) was polymerized with a 1:1 mixture of terephthaloyl and isophthaloyl chlorides (1.5988 g total, 0.007875 mole total), with p-phenoxybenzophenone (0.0686 g, 0.00025 mole) as a capping agent by the procedure of Example 4. The amounts of aluminum chloride and DMF used were 9.20 g (0.069025 mole) and 2.43 mL (0.0315 mole), respectively.

A yield of 4.87 g (97.6%) of fibrous white polymer with repeat unit

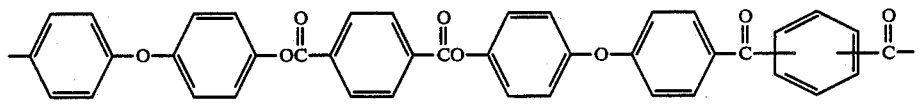

was obtained. Its reduced viscosity in o-chlorophenol was 0.36 (some undissolved material). It could be pressed into a brittle slab at 250° C.

EXAMPLE 13

4,4'-Bis-(p-phenoxy)azobenzene was prepared as follows.

A solution of 4-nitrodiphenyl ether (26 g) in denatured alcohol (100 mL) was added over 15 min to a stirred mixture of potassium hydroxide (60 g), water (100 mL), denatured alcohol (200 mL), and zinc dust (45 g). The mixture was refluxed overnight.

Methanol (1100 mL) was added. The reaction mixture was heated to boiling and filtered to remove the zinc dust. The product was isolated by evaporation of the filtrate to dryness. The crude yield was 16 g (78%). It purified by recrystallization from denatured alcohol.

EXAMPLE 14

4,4'-Bis-(p-phenoxy)azobenzene (3.7008 g, 0.0101 mole) from Example 13 was polymerized with terephthaloyl chloride (2.0303 g, 0.0100 mole) by the procedure of Example 4. The amounts of aluminum chloride and DMF used were 8.80 g (0.0660 mole) and 3.08 mL (0.0400 mole), respectively. After 2 hours at room temperature a further 2.67 g (0.02 moles) aluminum chloride was added and the reaction mixture left at room temperature for another 4 hours. The fibrous tan colored polymer which was obtained had the repeat unit

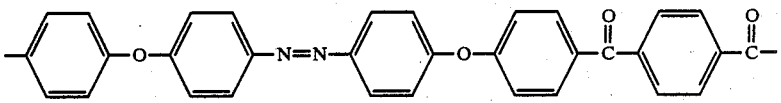

The polymer was partly soluble in concentrated sulfuric acid, RV 0.76 dl/g.

EXAMPLE 15

N,N'-Bis-(4-phenoxyphenyl)-3,3',4,4'-benzophenone tetracarboxylic di-imide (BPBPTCDI) was prepared was follows.

3,3',4,4'-benzophenone tetracarboxylic acid dianhydride (BPTCDA) (Aldrich, 96% purity) was purified by Soxhlet extraction with 2-butanone to yield a pale straw crystalline powder (DSC purity 99.76%; mp 223.7°–225.2° C.).

p-Phenoxyaniline (purified as described in Example 5, 19.45 g, 0.105 mole) was stirred at 150° C. with BPTCDA (16.11 g, 0.05 mole) in glycerol (200 mL) for 6.5 hours. The hot (100° C.) reaction mixture was poured into 1250 mL stirred water, then vacuum filtered. The yellow product was washed with water, denatured alcohol, and ether until the washings were colorless, then dried at 110° C. for 30 minutes under vacuum (yield 30.36 g, 92.5%).

10 g of the BPBPTCDI were washed by stirring with 300 mL DMAc at 100° C., then filtered and dried at 140° C. under vacuum for 6 hours to yield 6.67 g of a bright yellow powder, mp 316–18 by DSC.

Elemental analysis: Calc. C 74.99, H 3.68, N 4.27; Found C 75.06, H 3.80, N 4.28; Found C 75.08, H 3.80, N 4.25.

EXAMPLE 16

BPBPTCDI was polymerized with a 7:3 mixture of iso- and terephthaloyl chlorides as follows.

The general procedure of Example 4 was followed, using the following materials: BPBPTCDI (0.0150 mole, 9.8498 g), terephthaloyl chloride (0.0046 mole, 0.9319 g), isophthaloyl chloride (0.0107 mole, 2.1744 g vacuum distilled and recrystallized from hexane, mp 42.5°–43.8° C., DSC purity 99.75%), 4-phenoxybenzophenone (capping agent, 0.0006 mole, 0.1646 g), DMF (0.0612 mole, 4.71 mL), aluminum chloride (0.1842 mole, 24.56 g), and DCE (120 mL). The acid chlorides were added at −26° C. The mixture was dark brown. The temperature was held between −14° C. and −7° C. for 2 hours during which time hydrogen chloride was slowly and steadily evolved and the mixture gelled. The polymer complex was then left overnight at +7° C. and the tough rubbery dark brown complex was then worked up in methanol to give a lemon yellow fibrous polymer. This was boiled in methanol for 3 hours then washed with ether, filtered, and dried at 140° C. for 2 hours under vacuum to yield 11.28 g (94%) of a polymer having the repeat unit

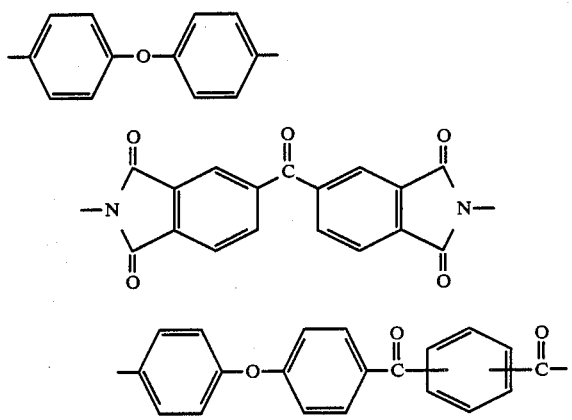

The polymer had an inherent viscosity of 1.68. It was partially soluble, with difficulty, in hot o-chlorophenol.

It had the following physical properties: Tg (Dynamic mechanical analysis (DMA))=224° C. (disc pressed at 380° C.), tensile storage modulus (DMA, 20° C.)=2750 MPa (400000 psi)

Elemental analysis: Calc. C 74.92, H 3.35, N 3.50; Found C 74.34, H 3.47, N 3.56; Found (with $WO_3$) C 75.25, H 3.53, N 3.54.

Al residue determined by atomic absorption spectroscopy was 320 ppm.

X-ray diffraction showed crystallinity (up to 30%), and DSC showed a crystallization exotherm at 225°–275° C. and a melting endotherm at 350°–390° C.

| TGA (10 C./minute) | 1% wt loss in air at 490° C. |
|---|---|
| | 1% wt loss in $N_2$ at 520° C. |

Analysis of thermogravimetric curves at 2.5°, 5°, 10° and 20° C./minute (assuming first order degradation kinetics) gave the following parameters:

Activation energy, E = 145 kJ/mol

Pre-exponential factor, A = 2.7E + 07 per minute

These values predict a 1% wt loss after 60 minutes at 402° C.

EXAMPLE 17 p-Phenoxybenzoyl chloride (36.77 g, 0.158 mole) was added at room temperature to a stirred solution of hexamethylene diamine (8.75 g, 0.075 mole) in DMAc (230 mL). The temperature of the reaction mixture rose to about 75° C. and a white precipitate formed. After standing overnight the mixture was heated at 100° C. for 1 hour, allowed to cool then poured into a stirred mixture of 200 mL sodium hydroxide (1N) and water (1 L). The product 1,6-bis-(4-phenoxybenzamido)-n-hexane (28.3 g, 74% yield) was recrystallized from a mixture of 200 mL denatured alcohol and 150 mL DMAc, filtered, washed with denatured alcohol, and dried under vacuum at 140° C. for 6 hours. The DSC purity was 99.91%, mp 183°–184.3° C.

1,6-Bis-(4-phenoxybenzamido)-n-hexane (3.9672 g, 0.0078 moles) was polymerized with terephthaloyl chloride (1.5633 g, 0.0077 moles) by the procedure of Example 4. The amounts of aluminum chloride and DMF used were 9.07 g (0.068 moles) and 2.37 mL (0.0308 moles), respectively. The white fibrous polymer which was obtained (4.6 g, 92.6% yield) had the repeat unit

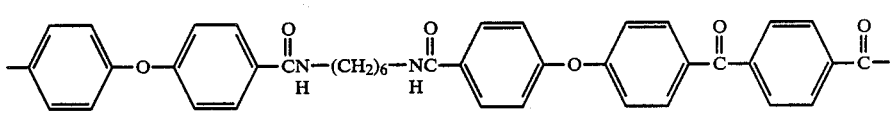

and dissolved quite readily in concentrated sulfuric acid to give a clear yellow solution. RV=2.18 dl/g; IV=1.97 dl/g. It could be pressed to a slab at 250° C. DMA indicated a Tg at 167° C. and a possible mp at about 330° C. DSC showed a broad Tg around 70° C., a crystallization exotherm at 300° C. and a melting endotherm at 354° C. (63 J/g). TGA in nitrogen indicated a 1% loss at 410° C. (335° C. in air). X-ray diffraction indicated about 20% crystallinity.

Elemental analysis: Calc. C 74.36, H 5.35, N 4.40; Found C 77.38, H 5.45, N 4.36

EXAMPLE 18

Bis-(p-phenoxyphenol) isophthalate was prepared from p-phenoxyphenol and isophthaloyl chloride by the method of Example 7. The product was obtained in 91.8% yield and recrystallized from a 2.5:1 v/v chlorobenzene-hexane (DSC purity 99.72%, mp 147.1°–148.6° C.).

This ester (10.5530 g, 0.0210 moles) was polymerized with terephthaloyl chloride (4.3244 g, 0.02130 moles) using the procedure of Example 16. p-Phenoxybenzophenone (0.1646 g, 0.0006 moles) was used as a capping agent. The amounts of aluminum chloride and DMF used were 25.000 g (0.1875 moles) and 6.56 mL (0.0852 moles), respectively. The white fibrous polymer which was obtained had the repeat unit

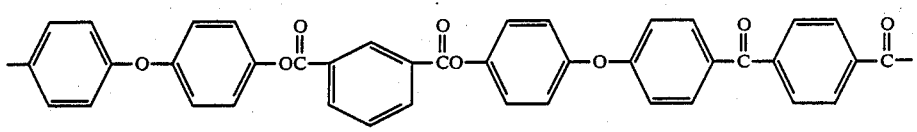

It was insoluble in many common solvents but did dissolve in 98% sulfuric acid to give a clear golden

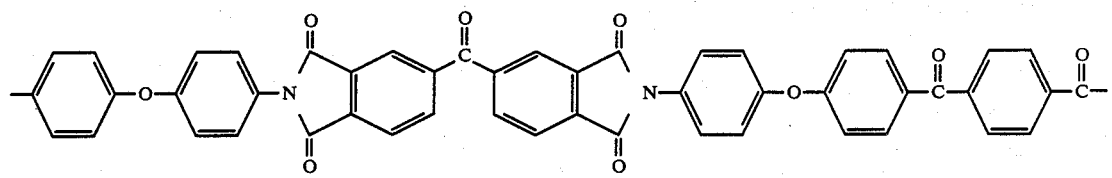

orange solution, but IV measurements showed that it rapidly degraded therein: IV after 14 minutes, 0.23; after 59 minutes, 0.11 dl/g. DSC indicated a Tg at 174° C. and two sharp melting endotherms at 330–350 and 350°–362° C.

Elemental analysis: Calc. C 76.03, H 3.83; Found C 77.66, H 3.89, N 0.03

EXAMPLE 19

Bis-4,4'-(p-phenoxy)azobenzene (5.7894 g, 0.0158 moles) was polymerized with isophthaloyl chloride (3.2484 g, 0.0160 moles) using the procedure of Example 14. p-Phenoxybenzophenone (0.1097 g, 0.0004 moles) was used as a capping agent. The amounts of aluminum chloride, DMF and DCE used were 16.45 g (0.1234 moles), 4.93 mL (0.0640 moles) and 64 mL, respectively. After ninety minutes a further 6 g of aluminum chloride was added and the mixture left stirring for fifteen hours. The fibrous orange polymer which was obtained (7.76 g, 97.2% yield; IV, 0.81 dl/g) had the repeat unit

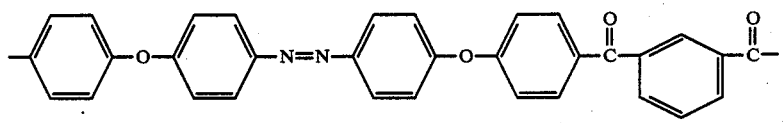

DSC crystallization exotherms were observed at 190–220 and 255°–270° C., along with an endotherm at 290°–310° C. C-13 NMR was consistent with the above structure.

EXAMPLE 20

BPBPTCDI (9.8498 g, 0.0150 moles) was polymerized with terephthaloyl chloride (3.1063 g, 0.0153 moles) using the other materials and the procedure of Example 16. The lemon yellow fibrous polymer obtained was completely soluble in concentrated sulfuric acid (IV 1.45 dl/g). DSC showed a Tg at about 250° C. but no Tc or Tm up to 400° C. TGA analysis indicated a 1% weight loss in nitrogen at 511° C. (480° C. in air). It had the repeat unit

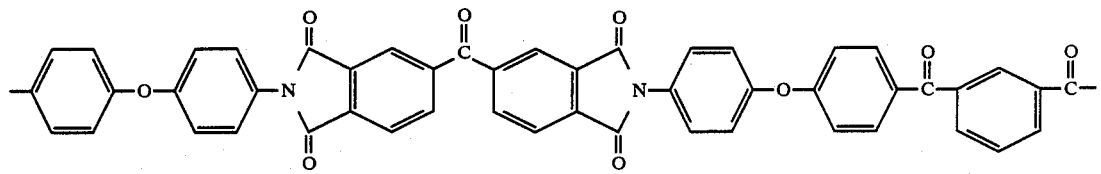

EXAMPLE 21

Example 20 was repeated using isophthaloyl chloride instead of terephthaloyl chloride. The lemon yellow fibrous polymer (11.48 g, 95.6% yield) which was obtained was completely soluble in concentrated sulfuric acid (IV 1.12 dl/g). DSC showed a Tg at 215° C., a crystallization exotherm at 260°–320° C. (maximum 302° C.) and a melting endotherm at 340°–370° C. (maximum 358° C.). TGA analysis indicated a 1% loss in nitrogen at 486° C. (459° C. in air). It had the repeat unit

EXAMPLE 22

Example 20 was repeated using a 1:1 w:w mixture of isophthaloyl and terephthaloyl chlorides. The lemon yellow fibrous polymer was completely soluble in concentrated sulfuric acid (IV 1.09 dl/g). DSC showed a Tg at 220° C., a crystallization exotherm at 240°–280° C. (maximum 255° C.) and a melting endotherm at 360°–390° C. (maximum 382° C.). TGA analysis indicated a 1% loss in nitrogen at 507° C. (469° C. in air).

EXAMPLE 23

Example 20 was repeated using a 3:7 w:w mixture of isophthaloyl and terephthaloyl chlorides. The lemon yellow fibrous polymer was completely soluble in concentrated sulfuric acid (IV 0.79 dl/g). DSC showed a Tg at 219° C., a crystallization exotherm at 230°–280° C. (maximum 248° C.) and a melting endotherm at 350°–390° C. (maximum 381° C.). TGA analysis indicated a 1% loss in nitrogen at 502° C. (465° C. in air).

EXAMPLE 24

Example 16 was repeated except that a mixture of BPBPTCDI (1.9700 g, 0.0030 moles) and 4,4'-diphenoxybenzophenone (4.3970 g, 0.0120 moles) was used. The resultant copolymer had repeat units of the structures

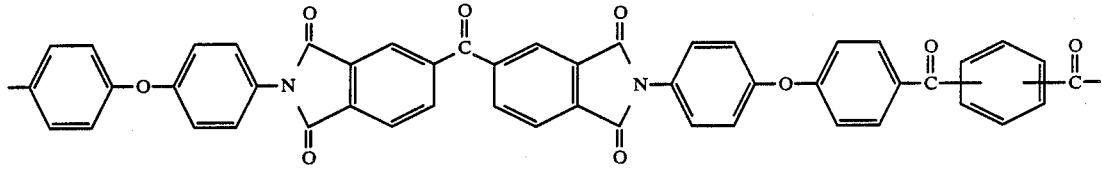

and

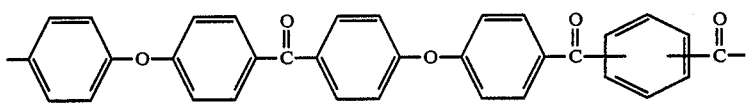

DSC showed a Tg at 189° C. and a melting endotherm at 320°-360° C. (maximum 348° C.). TGA analysis indicated a 1% loss in nitrogen at 513° C. (473° C. in air).

Elemental analysis: Calc. C 78.47, H 3.87, N 0.99; Found C 77.78, H 3.88, N 1.02

EXAMPLE 25 p-Phenoxybenzoyl chloride (12.633 g, 0.0543 moles) and BPBPTCDI (3.5459 g, 0.0054 moles) were polymerized with terephthaloyl chloride (1.1572 g, 0.0057 moles) in the presence of aluminum chloride (32.84 g, 0.2463 moles), DMF (10.08 mLs, 0.1308 moles), p-phenoxybenzophenone (0.1646 g, 0.0006 moles) and DCE (120 mLs) initially at −30° C., but warming to room temperature over two hours. The reaction mixture was left at room temperature for fifteen hours and then heated at 28°-32° C. for twenty-six hours. After working up as described in Example 4 the copolymer was obtained as a very pale orange fibrous powder (14.33 g, 95.2% yield), IV 0.90 dl/g (c=0.12 g/dL).

DSC showed a Tg at 178° C. and a melting endotherm at 300°-370° C. (maximum 340° C.). TGA analysis indicated a 1% loss in nitrogen at 430° C. (424° C. in air).

Elemental analysis: Calc. C 78.26, H 3.89, N 1.01; Found C 78.45, H 3.98, N 1.05

EXAMPLE 26

Bis-(p-phenoxyphenyl)diphenyl-6,6'-biquinoxaline (BPDPBQ) was prepared as follows.

p-Phenoxybenzil (12.06 g, 0.0400 moles) and 3,3'-diaminobenzidine (4.00 g, 0.0187 moles) were dissolved in chloroform and the solution boiled under reflux for 18 hours. The reaction mixture was filtered into 1 liter denatured alcohol and the precipitate separated, washed with denatured alcohol, and dried in vacuum at 100° C. for 2 hours (yield 12.05 g, 86%). The BPDPBQ was dissolved in boiling toluene (220 mL). The solution was filtered and denatured alcohol (125 mL) was added to the filtrate, which was then allowed to cool. The resulting fine yellow precipitate was filtered off and dried. DSC together with proton and C-13 NMR analysis indicated that the product was essentially a mixture of the 2,3'-bis-(p-phenoxyphenyl)-2',3-diphenyl-, 2,2'-bis-(p-phenoxyphenyl)-3,3,-diphenyl-, and 3,3'-bis-(p-phenoxyphenyl)-2,2'-diphenyl-positional isomers.

To a stirred mixture of aluminum chloride (8.334 g, 0.0625 moles), DMF (1.76 mL, 0.0228 moles) and DCE (80 mL) at −22° C. were added a mixture of BPDPDQ (4.1825 g, 0.0056 moles), isophthaloyl chloride (1.1572 g, 0.0057 moles) and p-phenoxybenzophenone (0.0549 g, 0.002 moles) at the same temperature. The mixture was then maintained at −8° C. for 18 hours, then worked up in methanol. The resultant light yellow fibrous powder was boiled in 400 mL methanol for 2.5 hours. 125 mL of the methanol was distilled off and the polymer filtered off and dried to yield 4.57 g (92%) of a polymer having the repeat unit

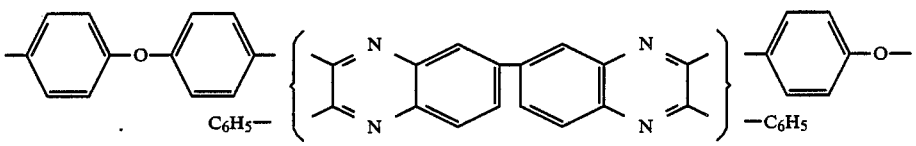

where

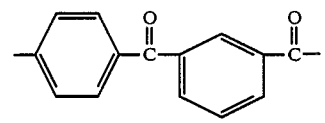

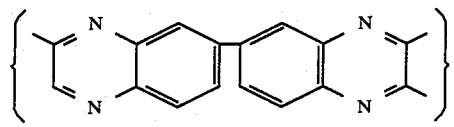

denotes the above-mentioned isomerism about the 2,2',3,3' positions.

The IV of the polymer was 1.29 dl/g. It was partially soluble in o-chlorophenol (IV 0.85 dl/gS). DSC analysis showed a Tg of about 224° C. TGA indicated a 1% loss in nitrogen at 479° C. (468° C. in air).

EXAMPLE 27

DMF (6.6 mL, 0.0852 moles) was added to a stirred and cooled mixture (which was kept below −20° C. until all the ingredients had been added) of aluminum chloride (24.95 g, 0.1874 moles) in DCE (120 mL). The bis-amide of Example 3 (10.5117 g, 0.210 moles) was then added, followed by p-phenoxybenzophenone (capping agent, 0.1646 g, 0.0006 moles) and isophthaloyl chloride (4.3243 g, 0.0213 moles). The reaction mixture was allowed to warm up to about 0° C. over on hour and maintained at this temperature for a further two hours, placed in a refrigerator at 5° C. overnight. Then the reaction mixture was worked up as described in Example 4. The white fibrous polymer which was obtained had the repeat unit

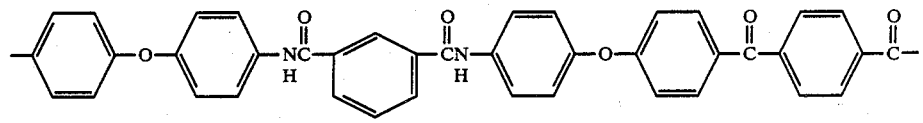

Its IV was 2.3 dl/g (c=0.09). Thermomechanical analysis TMA indicated the Tg to be 208° C.

EXAMPLE 28

N,N'-Bis-(4-phenoxyphenyl)isophthalamide was prepared by the reaction of p-phenoxyaniline with isophthaloyl chloride. This amide (10.5117 g, 0.0210 moles) was polymerized with terephthaloyl chloride (4.3243 g, 0.0213 moles) by the procedure of Example 27. The cream colored fibrous polymer which was obtained had the repeat unit

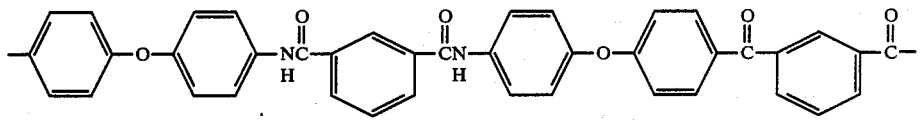

Its IV was 2.82 dl/g. Its Tg by TMA was 242° C.

EXAMPLE 29

Example 28 was repeated except that isophthaloyl chloride was used in place of terephthaloyl chloride in the polymerization. The light pink fibrous polymer which was obtained had the repeat unit

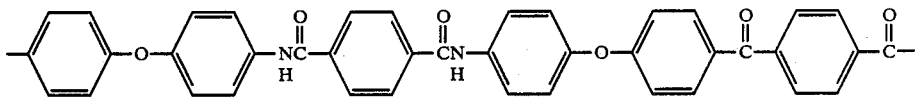

It had an IV of 2.79 dl/g.

EXAMPLE 30

Example 28 was repeated except that the corresponding terephthalamide was used. The light pink fibrous polymer which was obtained had the repeat unit.

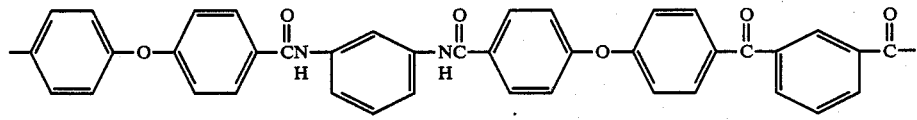

It had an IV of 3.32 dl/g. Its Tg by TMA was 242° C.

EXAMPLE 31

Example 27 was repeated except that the bis-amide of Example 1 was substituted for the bis-amide of Example 3. The white fibrous polymer which was obtained had the repeat unit

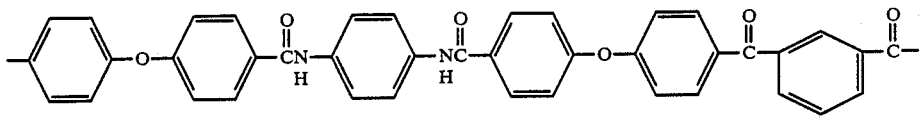

It had an IV of 2.99 dl/g.

EXAMPLE 32

Example 30 was repeated except that isophthaloyl chloride was used in place of terephthaloyl chloride in the polymerization. The pink fibrous polymer which was obtained had the repeat unit

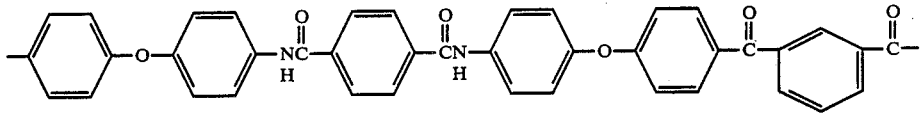

It had an IV of 3.15 dl/g.

EXAMPLE 33

N,N'-Di-(4-phenoxyphenyl)hexafluoroglutaramide was prepared by reaction of p-phenoxyaniline with hexafluoroglutaroyl chloride. This amide (6.0319 g, 0.0105) was polymerized with terephthaloyl chloride (2.1624 g, 0.01065 moles), with p-phenoxybenzophenone (0.1646 g, 0.0006 moles) as capping agent and using the procedure of Example 27. The amounts of aluminum chloride, DMF and DCE used were 12.49 g (0.0937 moles), 3.3 mL (0.0426 moles) and 50 mL, respectively. The polymer which was obtained as white powdery flakes had the repeat unit

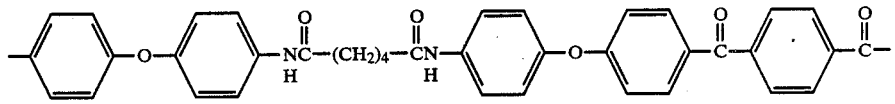

It had an IV of 1.97 dl/g.

EXAMPLE 34

The polymerization of Example 33 was repeated using isophthaloyl chloride in place of terephthaloyl chloride. The light pink polymer which was obtained had the repeat unit It had an IV of 1.27 dl/g.

EXAMPLE 35

N,N'-Bis-(4-phenoxyphenyl)adipamide was prepared by the reaction of p-phenoxyaniline with adipoyl chloride. This amide (5.8625 g, 0.0122 moles) was polymerized with terephthaloyl chloride (2.4969 g, 0.0123 moles) using p-phenoxybenzophenone (0.0825 g, 0.0003 moles) as capping agent and following the procedure of Example 27. The amounts of aluminum chloride, DMF and DCE used were 14.48 g (0.1086 moles), 3.79 mLs (0.0492 moles) and 60 mL, respectively. The light pink fibrous polymer which was obtained had the repeat unit

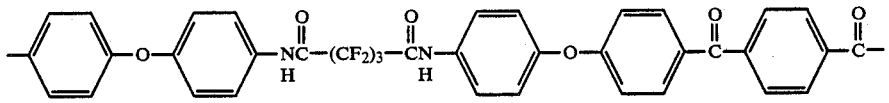

It had an IV of 1.56 dl/g.

EXAMPLE 36

N,N'-Bis-(4-phenoxyphenyl)-2,3,5,6-tetrafluoroterephthalamide was prepared from p-phenoxyaniline and 2,3,5,6-tetrafluoroterephthaloyl chloride. This amide (6.0108 g, 0.0105 moles) was polymerized with terephthaloyl chloride (2.1316 g, 0.0105 moles) by the procedure of Example 27. The amounts of aluminum chloride, DMF and DCE used were 12.55 g (0.094 moles), 3.3 mL (0.042 moles) and 60 mL, respectively. The white fibrous polymer which was obtained had the repeat unit

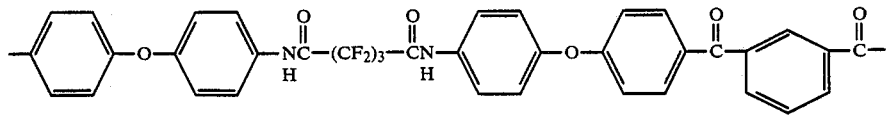

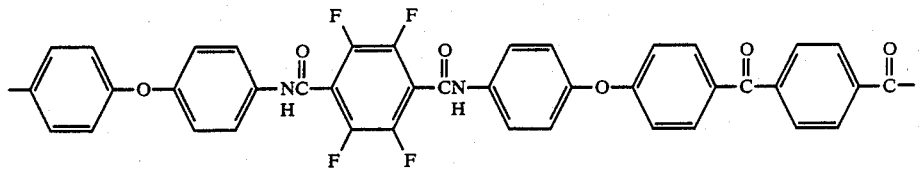

It had an IV of 0.83 dl/g.

EXAMPLE 37

N,N'-Bis-(4-phenoxyphenyl)-2,6-pyridine dicarboxamide was prepared from p-phenoxyaniline and 2,6-pyridine dicarboxylic acid dichloride. The amide (8.0248 g, 0.016 moles) was polymerized with isophthaloyl chloride (3.2484 g, 0.016 moles) using the procedure of Example 27. The amounts of aluminum chloride, DMF and DCE used were 21.33 g (0.160 moles), 4.71 mL (0.061 mol) and 100 mL, respectively. The off-white fibrous polymer which was obtained had the repeat unit

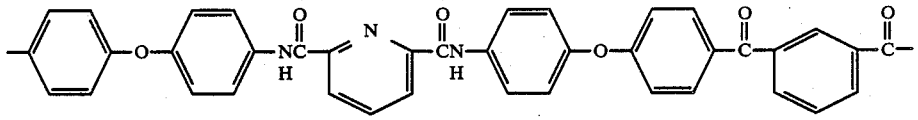

It dissolved readily in concentrated sulfuric acid (IV 0.7 dl/g).

EXAMPLE 38

N,N'-Bis-(4-phenoxyphenyl)pyromellitimide was prepared from p-phenoxyaniline and pyromellitic dianhydride. The imide (10.7745 g, 0.0195 moles) was polymerized with a 7:3 w:w mixture of isophthaloyl chloride (2.8140 g, 0.01386 moles) and terephthaloyl chloride (1.2060 g, 0.00594 moles) in the presence of p-phenoxybenzophenone (0.1647 g, 0.0006 moles) as a cappingg agent. The amounts of aluminum chloride, DMF and DCE used were 28.96 g (0.2172 moles), 6.15 mL (0.0792 moles) and 120 mL, respectively. The yellow fibrous polymer which was obtained had the repeat unit It dissolved completely in concentrated sulfuric acid (IV 1.46 dl/g).

EXAMPLE 39

The imide monomer of Example 38 (2.1549 g, 0.0039 moles) and 4,4'-diphenoxybenzophenone (5.7162 g, 0.0156 moles) were polymerized with terephthaloyl chloride (3.9589 g, 0.0195 moles). The amounts of aluminum chloride, DMF and DCE used were 28.96 g (0.2172 moles), 6.15 mL (0.0792 moles) and 120 mL. The yellow fibrous copolymer which was obtained had the repeat units

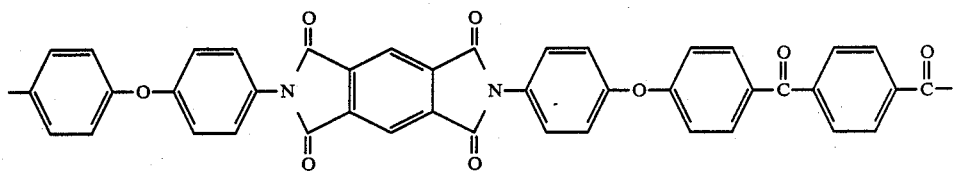

and

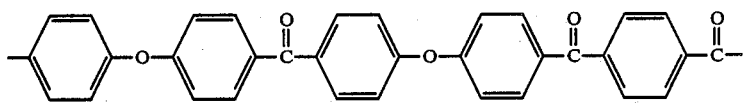

It dissolved completely in concentrated sulfuric acid (IV 1.68 dl/g).

EXAMPLE 40

N-(4-phenoxyphenyl)-1,2-dicarboximidobenzene-5-carboxylic acid chloride was prepared from p-phenoxyaniline and trimellitic anhydride followed by reaction with thionyl chloride. This imide-acid chloride (1.1501 g, 0.0345 moles) were polymerized by the procedure of example 27 except that no capping agent was used and lithium chloride (0.8521 g) was substituted for the DMF. The amounts of aluminum chloride and DCE used were 4.600 g (0.0345 moles) and 30 mLs, respectively. The polymer was obtained as yellow powdery flakes which was completely soluble in concentrated

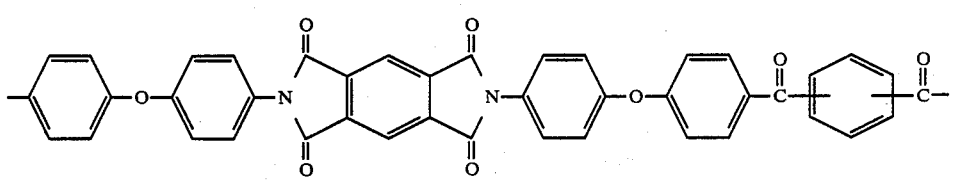

sulfuric acid (IV, 1.02 dl/g). The repeat unit had the structure

EXAMPLE 44

The bibenzimidazole of Example 43 is polymerized with terephthaloyl chloride to produce a polymer with the repeat unit

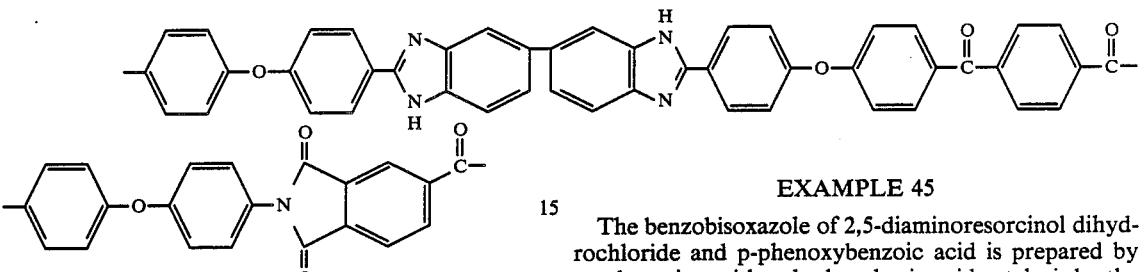

EXAMPLE 41

Following the procedure of Example 27, the bis-amide of Example 3 was polymerized with naphthalene-2-dicarbonyl dichloride to yield a polymer with IV 0.14 and repeat unit

EXAMPLE 45

The benzobisoxazole of 2,5-diaminoresorcinol dihydrochloride and p-phenoxybenzoic acid is prepared by condensation with polyphosphoric acid catalysis by the general procedure of Wolfe, Polym. Prep. 19 (2), 1 (1978) and then polymerized with terephthaloyl chloride, following the general procedure of Example 4, to produce a polymer having the repeat unit

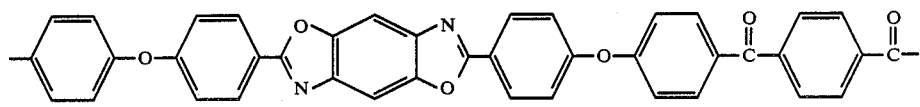

EXAMPLE 46

The benzobisthiazole of 2,5-diamino-1,4-benzenedithiol dihydrochloride and p-phenoxybenzoic acid is prepared by condensation with polyphosphoric acid catalysis by the general procedure of Wolfe, supra, and then polymerized with terephthaloyl chloride, following the general procedure of Example 4, to produce a polymer having the repeat unit

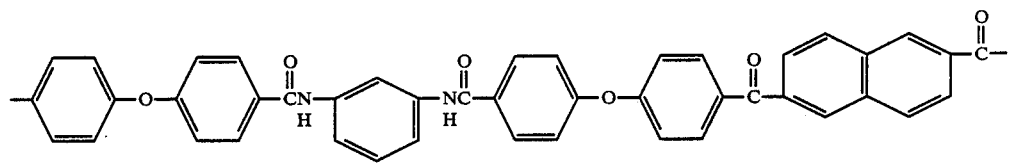

EXAMPLE 42

Following the procedure of Examples 3 and 27, the bis-amide of naphthalene-2,6-dicarbonyl dichloride and p-phenoxyaniline was prepared and polymerized with isophthaloyl chloride to yield a polymer with IV 0.29

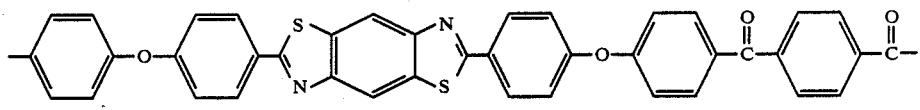

and repeat unit

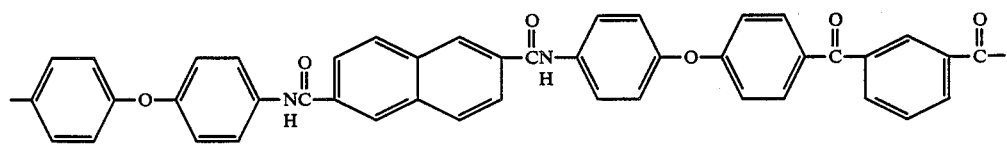

EXAMPLE 43

2,2'-Bis-(4-phenoxyphenyl)-5,5'-bibenzimidazole is prepared from 3,3'-diaminobenzidine and phenyl p-phenoxybenzoate in polyphosphoric acid.

EXAMPLE 47

4,4'-Azobis(benzoyl chloride) is polymerized with diphenyl ether following the general procedure of Example 4 to produce the polymer having the repeat unit

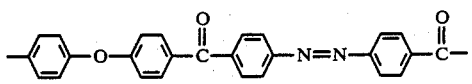

general procedure of Example 5. The bisimide is then polymerized with terephthaloyl chloride following the general procedure of Example 4, to produce a polymer with the repeat unit

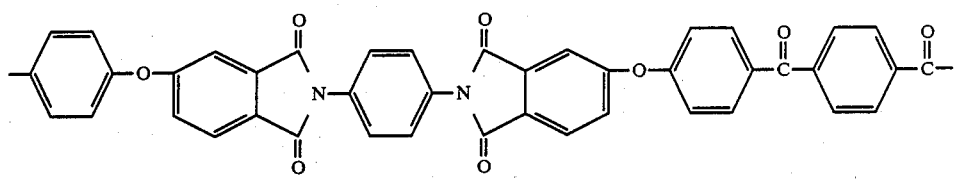

EXAMPLE 48

4,4′-Bis(p-phenoxy)azobenzene and 4,4′-azobis(benzoyl chloride) are polymerized following the general procedure of Example 4 to produce a polymer having the repeat unit

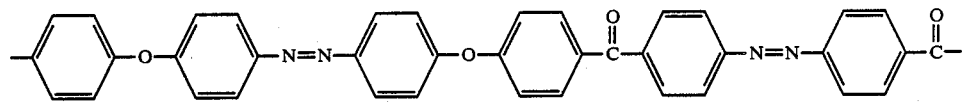

EXAMPLE 49

The mono p-phenoxyphenyl carboxamide of terephthaloyl chloride is prepared from p-phenoxyaniline and a large excess of terephthaloyl chloride, following the general procedure of Example 1. After treatment with thionyl chloride to reconvert to the acid chloride of any carboxylic acid groups produced by adventitious hydrolysis, the product is polymerized following the general procedure of Example 40 to produce a polymer having the repeat unit

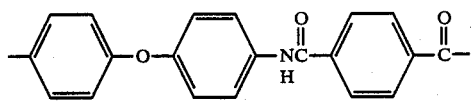

EXAMPLE 50

Following the general procedure of Heath et al., U.S. Pat. No. 3,956,320, 4-phenoxyphthalic anhydride is prepared by the condensation of 4-nitrophthalonitrile with sodium phenoxide, followed by hydrolysis and thermal dehydration. The anhydride is reacted with p-phenylene diamine to form the bisimide, following the general procedure of Example 5. The bisimide is then polymerized with terephthaloyl chloride following the general procedure of Example 4, to produce a polymer with the repeat unit

EXAMPLE 51

The imide of trimellitic anhydride and p-aminobenzoic acid is prepared and converted to the corresponding diacid chloride following the general procedures of Examples 5 and 40. The diacid chloride is polymerized with diphenyl ether by the general procedure of Example 4 to produce a polymer with the repeat unit

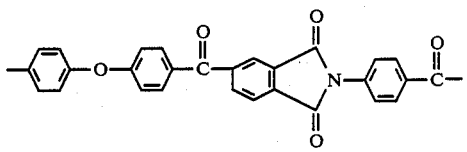

EXAMPLE 52

The bisimide of pyromellitic anhydride and p-aminobenzoic acid, prepared by the general procedure of Example 5 and converted to the corresponding diacid chloride with thionyl chloride, is polymerized with diphenyl ether following the general procedure of Example 4 to produce a polymer having the repeat unit

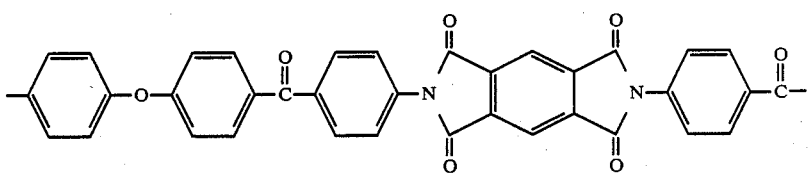

EXAMPLE 53

The bisimide of trimellitic anhydride and p-phenylene diamine, prepared by the general procedure of Example 5 and converted to the corresponding diacid chloride with thionyl chloride, is polymerized with diphenyl ether following the general procedure of Example 4 to produce a polymer having the repeat unit

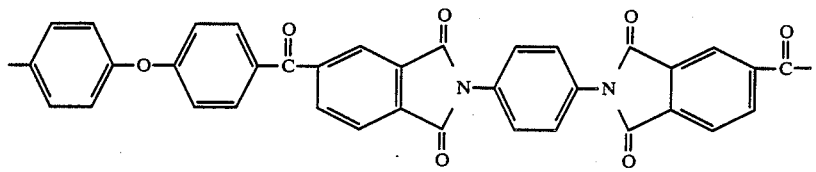

EXAMPLE 54

The imide of 4-phenoxyphthalic anhydride and p-aminobenzoic acid, prepared by the general procedure of Example 5 and converted to the corresponding acid chloride with thionyl chloride, is polymerized following the general procedure of Example 40 to produce a polymer having the repeat unit

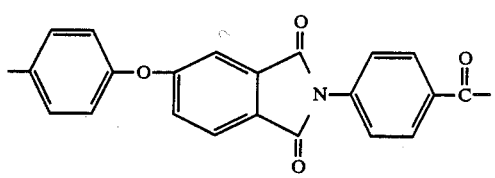

EXAMPLE 55

4,4'-Azobis(benzoyl chloride) is polymerized with 1,4-diphenoxybenzene following the general procedure of Example 4 to produce a polymer having the repeat unit

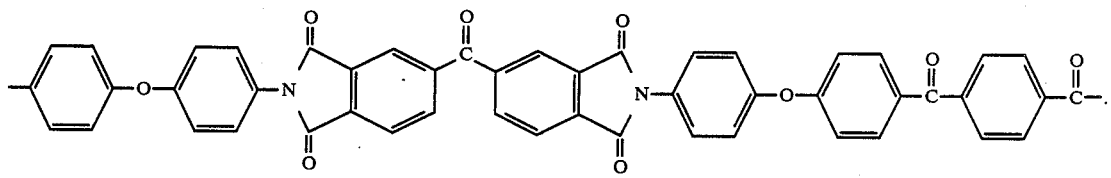

EXAMPLE 56

4,4'-Azobis(benzoyl chloride) is polymerized with 4-biphenylyl ether following the general procedure of Example 4 to produce a polymer having the repeat unit

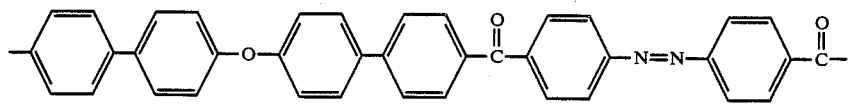

We claim:

1. A polymer having a repeat unit

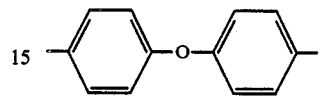

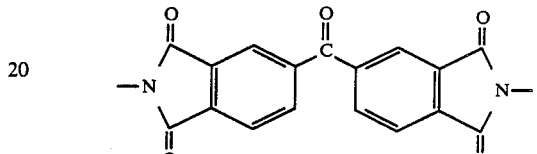

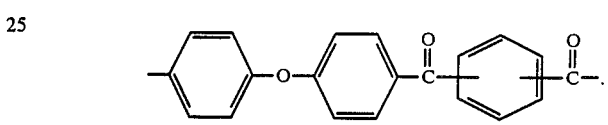

2. A polymer according to claim 1 having the repeat unit

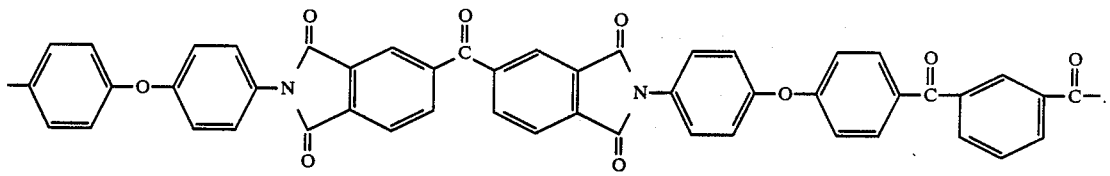

3. A polymer according to claim 1 having the repeat unit

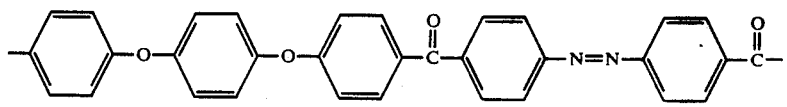

4. A polymer according to claim 1, 2, or 3 having an inherent viscosity of at least 0.6, measured at 25° C. with 0.1 g of polymer dissolved in 100 mL concentrated sulfuric acid.

* * * * *